US012447033B2

(12) United States Patent
Xia et al.

(10) Patent No.: US 12,447,033 B2
(45) Date of Patent: Oct. 21, 2025

(54) TELESCOPIC ADJUSTING STRUCTURE OF SUPPORT ARM AND KNEE BRACE

(71) Applicants: VINCENT MEDICAL (DONG GUAN) MANUFACTURING CO., LTD, Guangdong (CN); VINCENT MEDICAL (DONG GUAN) TECHNOLOGY CO., LTD, Guangdong (CN); REHAB-ROBOTICS COMPANY LIMITED, Hong Kong (CN)

(72) Inventors: Mingjun Xia, Guangdong (CN); Wei Liang, Guangdong (CN); Guofu Fu, Guangdong (CN); Jialin Cai, Guangdong (CN); Peiyong Xu, Guangdong (CN); Yongjian Chen, Guangdong (CN)

(73) Assignees: VINCENT MEDICAL (DONG GUAN) MANUFACTURING CO., LTD, Guangdong (CN); VINCENT MEDICAL (DONG GUAN) TECHNOLOGY CO., LTD, Guangdong (CN); REHAB-ROBOTICS COMPANY LIMITED, Hong Kong (CN)

( * ) Notice: Subject to any disclaimer, the term of this patent is extended or adjusted under 35 U.S.C. 154(b) by 263 days.

(21) Appl. No.: 18/199,665

(22) Filed: May 19, 2023

(65) Prior Publication Data

US 2023/0414393 A1 Dec. 28, 2023

(30) Foreign Application Priority Data

Jun. 22, 2022 (CN) ........................ 202210710026.X

(51) Int. Cl.
*A61F 5/01* (2006.01)

(52) U.S. Cl.
CPC .......... *A61F 5/0106* (2013.01); *A61F 5/0123* (2013.01)

(58) Field of Classification Search
CPC ............................. A61F 5/0106; A61F 5/0123
See application file for complete search history.

(56) References Cited

U.S. PATENT DOCUMENTS 6,821,261 B2 * 11/2004 Doty ..................... A61F 5/0125 602/5
7,988,653 B2 * 8/2011 Fout ........................ A61F 5/013 602/5

(Continued)

FOREIGN PATENT DOCUMENTS

CN 106264988 A 1/2017

*Primary Examiner* — Keri J Nelson
(74) *Attorney, Agent, or Firm* — MUNCY, GEISSLER, OLDS & LOWE, P.C.

(57) ABSTRACT

The present disclosure relates to the technical field of a rehabilitation protective gear, in particular to a telescopic adjusting structure of a support arm and a knee brace. The telescopic adjusting structure of the support arm comprises an adjusting arm and a support arm guard movably connected along the length direction, and further comprises a telescopic adjusting mechanism. The telescopic adjusting mechanism comprises a pushing component, which is movably provided on the support arm guard; a locking component, one end of which is connected with the pushing component, and the other end of which is clamped with the adjusting arm, wherein when the pushing component moves, the locking component is disengaged from or locked with the adjusting arm. The telescopic adjusting mechanism is provided, so that the extension length matching between the adjusting arm and the support arm guard is adjusted.

10 Claims, 11 Drawing Sheets

(56) References Cited

U.S. PATENT DOCUMENTS

| | | | | |
|---|---|---|---|---|
| 8,172,781 | B2 * | 5/2012 | Oddou | A61F 5/0125<br>602/61 |
| 9,925,082 | B2 * | 3/2018 | Chetlapalli | A61F 5/0123 |
| 9,993,362 | B2 * | 6/2018 | Costello | A61F 5/0123 |
| 10,524,948 | B2 * | 1/2020 | Santaniello | A61F 5/0102 |
| 2005/0059916 | A2 * | 3/2005 | Enzerink | A61F 5/0125<br>602/26 |
| 2020/0197209 | A1 * | 6/2020 | Bejarano | A61F 5/0125 |

* cited by examiner

TELESCOPIC ADJUSTING STRUCTURE OF SUPPORT ARM AND KNEE BRACE

CROSS-REFERENCE TO RELATED APPLICATION

This patent application claims the benefit and priority of Chinese Patent Application No. 202210710026.X filed with the China National Intellectual Property Administration on Jun. 22, 2022, the disclosure of which is incorporated by reference herein in its entirety as part of the present application.

TECHNICAL FIELD

The present disclosure relates to the technical field of a rehabilitation protective gear, in particular to a telescopic adjusting structure of a support arm and a knee brace.

BACKGROUND

Knee is one of the joints with large endurance of human body and a complex structure. Knee diseases often occur in daily life, which leads to limited human movement and seriously reduces the quality of life. In order to alleviate the injury of knee diseases to human body and improve the quality of life, a knee brace is provided in the prior art. A support structure (such as a support arm) is provided on the periphery of the knee to assist in supporting the bones associated with the knee and assist in fixing and supporting the knee, so as to provide powerful protective support for people with knee discomfort, alleviate the pain and discomfort of the knee, and provide walking support for some people with walking disabilities to a certain extent, thereby reducing the limited movement of human body and improving the quality of life to a certain extent.

However, when wearing a knee brace, it is necessary to adjust the length of the knee brace adaptively. However, for most patients with knee diseases, the self-care ability of daily living is greatly limited, which leads to the inconvenience of adjusting the length of the knee brace when a user wears the knee brace.

Therefore, the prior art has defects and deficiencies, which need to be further improved and developed.

SUMMARY

In view of the shortcomings of the prior art, the purpose of the present disclosure is to provide a telescopic adjusting structure of a support arm and a knee brace, aiming at solving the problem in the prior art that it is inconvenient to adjust the length of the knee brace.

The technical scheme used by the present disclosure to solve the technical problems is as follows: a telescopic adjusting structure of a support arm, which is used for a support arm of a knee brace and comprises an adjusting arm and a support arm guard movably connected along the length direction, wherein the telescopic adjusting structure further comprises a telescopic adjusting mechanism, and the telescopic adjusting mechanism comprises:

a pushing component, which is movably provided on the support arm guard;

a locking component, one end of which is connected with the pushing component, and the other end of which is clamped with the adjusting arm, wherein when the pushing component moves, the locking component is disengaged from or locked with the adjusting arm.

In the above embodiment, the telescopic adjusting mechanism is provided, so that the extension length matching between the adjusting arm and the support arm guard can be adjusted.

The telescopic adjusting mechanism is provided with the pushing component and the locking component, so that the position of the locking component is adjusted by the pushing component, and the adjusting arm is locked and fixed by the locking component. At the same time, the pushing component is provided on the support arm guard and is connected with the locking component, so that the relative positions of the support arm guard and the adjusting arm can be adjusted by the pushing component and the locking component. In this way, the pushing component can be operated so as to adjust the locking component to lock the adjusting arm, so that the length of the support arm of the knee can be adjusted conveniently and quickly.

Preferably, the telescopic adjusting mechanism further comprises:

a push button pressing block, wherein the support arm guard is provided with a pressing block slot hole, and the pushing component is provided in the pressing block slot hole;

wherein the support arm guard is provided with an arm long hole along the length direction, the adjusting arm is slidably connected in the arm long hole, the adjusting arm is provided with an adjusting long hole along the length direction, and one end of the locking component away from the pushing component is accommodated in the adjusting long hole.

In the above embodiment, the push button pressing block is provided, so that the pushing component can be conveniently and stably assembled on the support arm guard, that is to say, the pushing component and the locking component are assembled on the support arm guard. The arm long hole is provided, so that the adjusting arm can be extended into the arm long hole, the hole wall of the arm long hole limits the adjusting arm along the height direction and the width direction, and the telescopic adjusting mechanism limits the adjusting arm along the length direction. Specifically, the locking component sequentially extends into the adjusting long hole through the pressing block slot hole and the arm long hole, and limits the hole wall of the adjusting long hole along the length direction.

Preferably, the pushing component comprises:

a push button slider, which is slidably connected to the push button pressing block;

a push button resetting element, wherein a resetting element baffle is provided at the outer side of the pressing block slot hole, and the push button resetting element is provided between the push button slider and the resetting element baffle.

In the above embodiment, the push button slider is provided, so that the position of the locking component is adjusted conveniently. Specifically, the position of the locking component along the height direction is adjusted. The push button resetting element and the resetting element baffle are provided, so that the position of the push button slider can be reset by the push button resetting element, and the locking component can lock the adjusting arm.

Preferably, the push button pressing block comprises:

a pressing block frame body, which is provided in the pressing block slot hole;

a first arm guard connecting part, which is provided at one end of the pressing block frame body along the length direction;

a second arm guard connecting part, which is provided at the other end of the pressing block frame body along the length direction;

slider sliding rails, which are provided on two long sides of the pressing block frame body;

wherein the first arm guard connecting part and the second arm guard connecting part are both clamped with the support arm guard, and the pushing component is slidably connected with the slider sliding rail and is limited with the slider sliding rail along the upward direction in the height direction.

In the above embodiment, the pressing block frame body is clamped on the support arm guard by the first arm guard connecting part and the second arm guard connecting part. The push button slider is slidably connected with the slider sliding rail, and the slider sliding rail is limited to move upward along the height direction, so that the slider sliding rail is prevented from separating upward from the slider sliding rail along the height direction, and it is convenient to push the push button slider and adjust the relative position of the locking component.

Preferably, the locking component comprises:

a push button stopper, one end of which is connected with the push button slider, and the other end of which is clamped with the adjusting arm;

a push button stopper pin, which is provided on the push button slider and is clamped with the push button slider.

In the above embodiment, the push button stopper is provided, so that the adjusting arm is clamped and fixed by the push button stopper. At the same time, the relative position of the push button stopper with respect to the adjusting arm can be adjusted by the pushing component, so that the adjusting arm is in a locked state or a free state along the length direction. The push button stopper pin is provided, so that the push button stopper can be connected with the push button slider, and the relative position of the push button stopper can be conveniently adjusted by the push button slider.

Preferably, the push button slider comprises:

a slider body;

a stopper accommodating groove, wherein the stopper accommodating groove is provided at one end of the slider body facing the push button stopper, and one end of the push button stopper is clamped with the stopper accommodating groove;

a pressing block sliding rail, which is provided at both sides of the stopper accommodating groove and is slidably connected with the slider sliding rail;

a resetting element fixing part, wherein the resetting element fixing part is provided on the slider body, and the push button resetting element is provided between the resetting element fixing part and the resetting element baffle;

wherein groove walls at both sides of the stopper accommodating groove along the length direction are provided with stopper pin fixing holes, the push button stopper pin penetrates through the push button stopper, and both ends of the push button stopper pin are fixed in the stopper pin fixing holes.

In the above embodiment, the stopper accommodating groove is provided, and the stopper pin fixing hole is provided thereon, so that the push button stopper pin can be connected with the push button stopper, which provides a guarantee for conveniently adjusting the relative position of the locking component. The pressing block sliding rail is provided, so that the relative sliding between the slider body and the support arm guard is convenient, and the moving track of the slider body is limited. It is ensured that the relative positional relationship between the locking component and the adjusting arm is effectively adjusted, and it is convenient to adjust the length of the knee brace. Preferably, the pushing component further comprises a push button slider cover, and the push button slider cover comprises:

a cover body;

a pushing end, which is provided at one end of the cover body away from the resetting element baffle along the length direction and is provided with skidproof stripes;

a slider accommodating groove, which is provided at one end of the cover body facing the support arm guard;

a plurality of slider clamping blocks, which are provided at the inner groove wall of the slider accommodating groove;

a slider latch, wherein the slider latch is provided at the groove wall of the slider accommodating groove close to the pushing end, the push button slider further comprises a cover body clamping groove provided at one side of the slider body away from the resetting element fixing part, and the slider latch is clamped with the cover body clamping groove;

wherein the plurality of slider clamping blocks cooperate with the slider latch to clamp and fix the cover body and the slider body.

In the above embodiment, the push button slider cover is provided, so that it is further convenient to operate the push button slider to adjust the positional relationship of the push button stopper with respect to the adjusting arm, which provides a guarantee for conveniently adjusting the length of the knee brace. The slider accommodating groove, the slider clamping block and the slider latch are provided, so that the push button slider can be conveniently accommodated, and the push button slider cover can be prevented from accidentally falling off, thus ensuring the connection stability of the push button slider cover.

Preferably, the push button stopper comprises:

a slider connecting end;

a limiting end, which is integrally formed with the slider connecting end;

wherein the adjusting arm is provided with an adjusting long hole along the length direction, a plurality of limiting parts and accommodating parts are provided in the adjusting long hole at intervals, the size of the limiting parts is smaller than that of the accommodating parts along the width direction; the size of the slider connecting end along the width direction is smaller than that of the limiting part along the width direction, and the size of the limiting part along the width direction is smaller than that of the limiting end along the width direction; the slider connecting end is provided with a stopper pin sliding chute hole, and the height of one side of the stopper pin sliding chute hole away from the resetting element baffle is lower than that of one side of the stopper pin sliding chute hole close to the resetting element baffle; and the push button stopper pin is slidably connected in the stopper pin sliding chute hole.

In the above embodiment, the adjusting arm is provided with an adjusting long hole, and a plurality of limiting parts and accommodating parts provided at intervals are provided in the adjusting long hole, so as to control the size relationship between the limiting parts and accommodating parts along the width direction, and the size relationship between the slider connecting end and the limiting end and the limiting parts along the width direction. Further, the slider connecting end can pass through the limiting part, but the limiting end cannot pass through the limiting part. That is to say, the adjusting arm is locked and limited along the length direction through the cooperation of the limiting end and the limiting part, and the free movement of the adjusting arm along the length direction can be opened through the slider connecting end. The stopper pin sliding chute hole is provided, so that the inclination angle of the stopper pin sliding chute hole is controlled. In cooperation with the push button stopper pin, the displacement of the push button slider along the length direction is transmitted to the push button stopper, and the push button stopper moves up and down along the height direction, so as to adjust the positional relationship of the slider connecting end and the limiting end with respect to the limit part, and further adjust the push button stopper to lock the adjusting arm, which provides a guarantee for conveniently adjusting the length of the knee brace.

Preferably, the support arm guard further comprises:

an arm guard body, wherein the arm long hole and the pressing block slot hole are both provided on the arm guard body, and the pressing block slot hole is communicated with the arm long hole;

a stopper resetting and fixing cantilever, wherein the stopper resetting and fixing cantilever is located on the arm guard body below the pressing block slot hole, and a U-shaped slot hole is provided between the stopper resetting and fixing cantilever and the arm guard body;

wherein the stopper resetting and fixing cantilever is provided with a threaded counterbore, some of the limiting ends away from the slider connecting end extend with cantilever connecting parts, the cantilever connecting parts abut against the threaded counterbore, and the cantilever connecting parts are screwed with the threaded counterbore by screws.

In the above embodiment, the stopper resetting and fixing cantilever is provided, and a U-shaped slot hole is controlled to be provided between the stopper resetting and fixing cantilever and the arm guard body, so that the stopper resetting and fixing cantilever has a certain elastic deformation ability. The limiting end extends out of the cantilever connecting parts, and the cantilever connecting parts are screwed with the threaded counterbore of the stopper resetting and fixing cantilever, so that the pushing component and the locking component are fixed between the push button pressing block and the stopper resetting and fixing cantilever along the height direction, and the push button resetting element and the stopper resetting and fixing cantilever cooperate to push the push button stopper and the push button slider to reset and lock the adjusting arm.

Another technical scheme used by the present disclosure to solve the technical problems is as follows: a knee brace, comprising two telescopic adjusting structures of the support arms as described above.

In the above embodiment, the knee brace uses the telescopic adjusting structure of the support arm in the above embodiment, so as to conveniently and quickly adjust the length of the knee brace.

Beneficial Effects

According to the telescopic adjusting structure of the support arm provided by the present disclosure, the telescopic adjusting mechanism is provided, so that the extension length matching between the adjusting arm and the support arm guard can be adjusted. The telescopic adjusting mechanism is provided with the pushing component and the locking component, so that the position of the locking component is adjusted by the pushing component, and the adjusting arm is locked and fixed by the locking component. At the same time, the pushing component is provided on the support arm guard and is connected with the locking component, so that the relative positions of the support arm guard and the adjusting arm can be adjusted by the pushing component and the locking component. In this way, the pushing component can be operated so as to adjust the locking component to lock the adjusting arm, so that the length of the support arm of the knee can be adjusted conveniently and quickly.

DESCRIPTION OF REFERENCE NUMERALS

Figure 1:
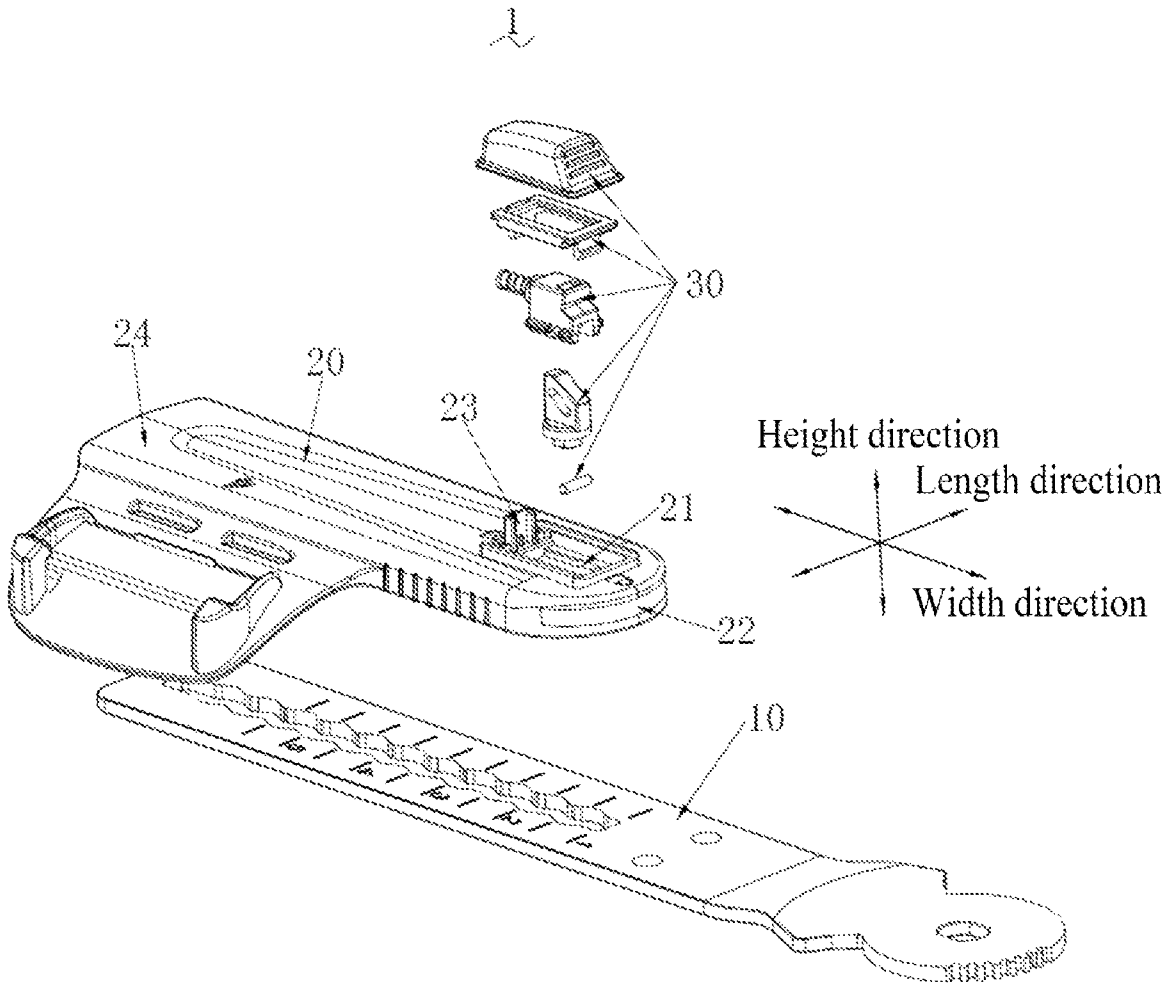
FIG. 1 is a three-dimensional explosion schematic diagram of a telescopic adjusting structure of a support arm according to the present disclosure.

100. Knee brace; 1. Telescopic adjusting structure of a support arm; 10. Adjusting arm; 20. Support arm guard; 30.

Telescopic adjusting mechanism; 11. Adjusting long hole; 111. Limiting part; 112. Accommodating part; 113. Scale identification; 21. Pressing block slot hole; 22. Arm long hole; 23. Resetting element baffle; 24. Arm guard body; 25. Stopper resetting and fixing cantilever; 26. U-shaped slot hole; 27. Threaded counterbore; 31. Pushing component; 32. Locking component; 33. Push button pressing block; 311. Push button slider; 312. Push button resetting element; 313. Push button slider cover; 3111. Slider body; 3112. Block accommodating groove; 3113. Pressing block sliding rail; 3114. Resetting element fixing part; 3115. Stopper pin fixing hole; 3116. Cover body clamping groove; 3131. Cover body; 3132. Pushing end; 3133. Slider accommodating groove; 3134. Slider clamping block; 3135. Slider latch; 3136. Skidproof stripe; 321. Push button stopper; 322. Push button stopper pin; 3211. Slider connecting end; 3212. Limiting end; 3213. Stopper pin sliding chute hole; 3214. Cantilever connecting part; 331. Pressing block frame body; 332. First arm guard connecting part; 333. Second arm guard connecting part; 334. Slider sliding rail.

DETAILED DESCRIPTION OF THE EMBODIMENTS

In order to make the purpose, technical scheme and advantage of the present disclosure clear and definite, the present disclosure will be further described in detail with reference to the attached drawings and embodiments. It should be understood that the specific embodiments described herein are only used to explain the present disclosure, rather than limit the present disclosure.

In the description of the present disclosure, it should be understood that the orientational or positional relationships indicated by the terms such as "center", "longitudinal", "transverse", "up", "down", "front", "back", "left", "right", "vertical", "horizontal", "top", "bottom", "inside", "outside" are based on the orientational or positional relationships shown in the figures only for the convenience of describing the present disclosure and simplifying the description, rather than indicate or imply that the referred devices or elements must have a specific orientation, be constructed and operated in a specific orientation, and therefore should not be construed as limiting the present disclosure. In addition, the terms such as "first" and "second" are only used for the purpose of description, and cannot be understood as indicating or implying relative importance or implicitly indicating the number of indicated technical features. Therefore, the features defined with "first" and "second" can include one or more of these features explicitly or implicitly. In the description of the present disclosure, "a plurality of" means two or more unless otherwise specified.

In the description of the present disclosure, it should be noted that unless otherwise specified and defined expressly, the terms such as "mount", "link" and "connect" should be understood broadly, for example, it can be fixed connection, detachable connection or integral connection; or mechanical connection or electrical connection; or direct connection or indirect connection through an intermediate medium, or internal communication in two elements. For those skilled in the art, the specific meanings of the above terms in the present disclosure can be understood according to specific situations.

A knee brace is a commonly used rehabilitation protective gear for patients with knee diseases. The knee brace usually comprises a thigh support arm, an angle adjuster and a shank support arm which are connected in sequence. The thigh support arm binds and fixes the thigh of a user, while the shank support arm binds and fixes the shank of the user. The thigh support arm and the shank support arm assist the knee in supporting the weight of the user. The thigh support arm and the shank support arm are rotatably connected through the angle adjuster, which can further reduce the stress on the knee and is beneficial to improving the recovery speed of knee diseases of the user. It can be known that the length of the knee brace basically consists of the lengths of the thigh support arm and the shank support arm. The telescopic adjusting structure of the support arm according to the present disclosure is applied to the thigh support arm and the shank support arm, and then the lengths of the thigh support arm and the shank support arm are adjusted through the telescopic adjusting structure of the support arm, so as to achieve the purpose of conveniently and quickly adjusting the length of the knee brace. Refer to the following embodiments for details.

As shown in FIG. 1 to FIG. 4, in a first embodiment of the present disclosure, there is provided a telescopic adjusting structure 1 of a support arm. The telescopic adjusting structure 1 of a support arm is used for the support arm of the knee brace 100 and can adjust the length of the support arm of the knee brace 100. Specifically, the telescopic adjusting structure 1 of the support arm comprises an adjusting arm 10, a telescopic adjusting mechanism 30 and a support arm guard 20. The adjusting arm 10 and the support arm guard 20 are movably connected along the length direction. The telescopic adjusting mechanism 30 is connected with both the adjusting arm 10 and the support arm guard 20 along the height direction, so as to adjust the relative positional relationship between the adjusting arm 10 and the support arm guard 20 through the telescopic adjusting mechanism 30, and further adjust the length of the knee brace 100.

Specifically, the telescopic adjusting mechanism 30 comprises a pushing component 31 and a locking component 32. The pushing component 31 is movably provided on the support arm guard 20, that is to say, the pushing component 31 is provided on the support arm guard 20 and can displace with respect to the support arm guard 20 for a certain stroke. One end of the locking component 32 is connected with the pushing component 31, and the other end of the locking component 32 is clamped with the adjusting arm 10, that is to say, one end of the locking component 32 is used to lock the adjusting arm 10, and the other end of the locking component 32 is used to be connected with the pushing component 31, so that the pushing component 31 can be operated to adjust the locking component 32, thereby controlling the adjusting arm 10 to be locked. When the pushing component 31 moves, the locking component 32 is disengaged from or locked with the adjusting arm 10. It can be seen that the pushing component 31 is controlled so that the locking component 32 can be adjusted to lock the adjusting arm 10. That is to say, the locking component 32 locks the adjusting arm 10 or does not lock the adjusting arm 10, so that the adjusting arm 10 has a certain degree of freedom of movement.

It can be understood that the telescopic adjusting mechanism 30 is provided, so that the extension length matching between the adjusting arm 10 and the support arm guard 20 can be adjusted. The telescopic adjusting mechanism 30 is provided with the pushing component 31 and the locking component 32, so that the position of the locking component 32 with respect to the adjusting arm 10 is adjusted by the pushing component 31, so as to control whether the locking component 32 locks the adjusting arm 10. At the same time, the pushing component 31 is provided on the support arm guard 20 and is connected with the locking component 32, so that the positions of the support arm guard 20 and the adjusting arm 10 can be fixedly connected by the pushing component 31 and the locking component 32, and the relative positions of the support arm guard 20 and the adjusting arm 10 can be adjusted by the pushing component 31 and the locking component 32. In this way, the pushing component 31 is operated so as to adjust the locking component 32 to lock the adjusting arm 10, so that the length of the support arm of the knee can be adjusted conveniently and quickly.

Figure 2:
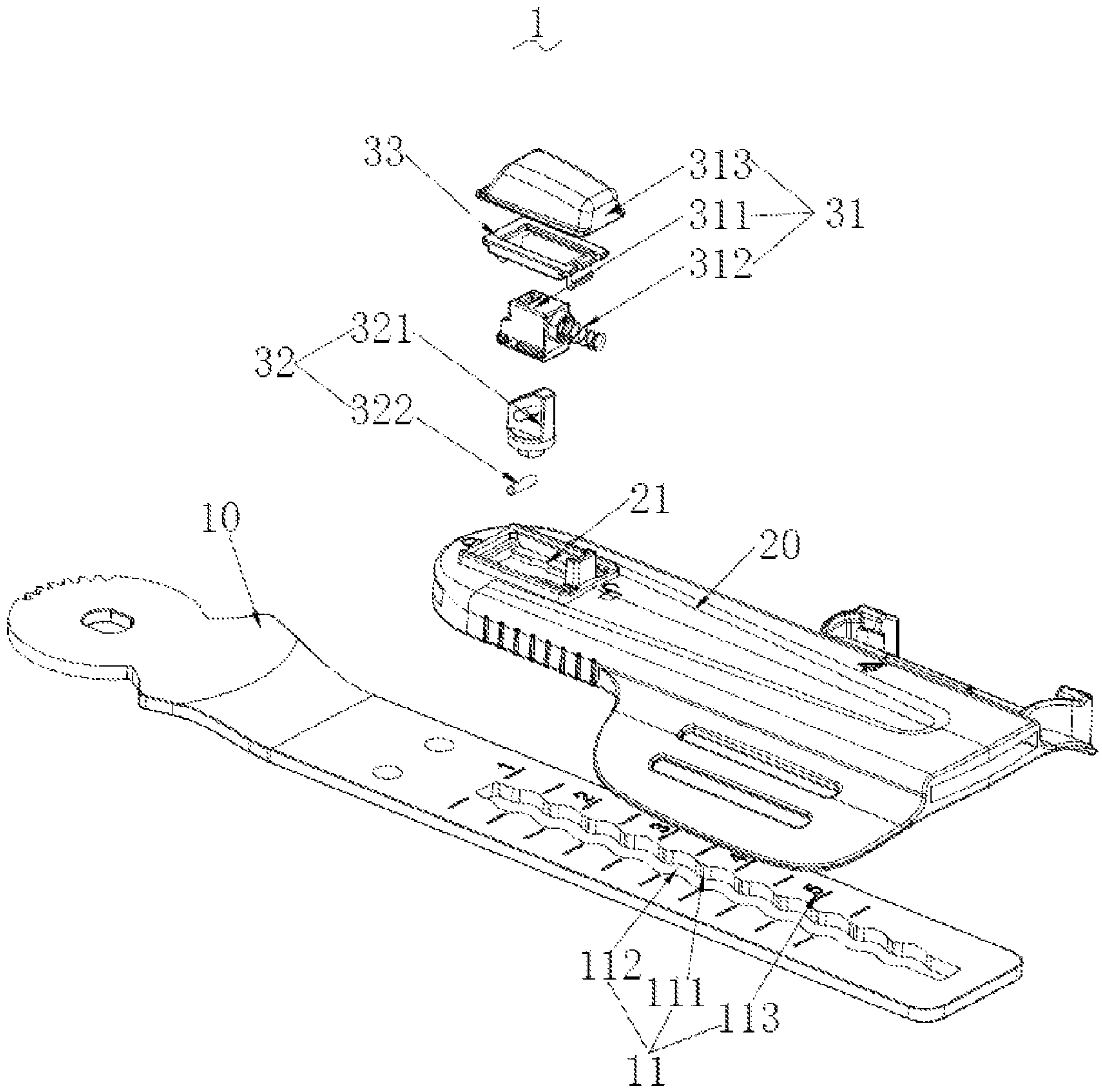
FIG. 2 is a three-dimensional explosion schematic diagram of a telescopic adjusting structure of a support arm according to the present disclosure from another perspective.

Further, as shown in FIGS. 1 and 2, in some embodiments, the telescopic adjusting mechanism 30 further comprises a push button pressing block 33. The support arm guard 20 is provided with a pressing block slot hole 21, and the pushing component 31 is provided in the pressing block slot hole 21, wherein the support arm guard 20 is provided with an arm long hole 22 along the length direction, the adjusting arm 10 is slidably connected in the arm long hole 22, the adjusting arm 10 is provided with an adjusting long hole 11 along the length direction, and one end of the locking component 32 away from the pushing component 31 is accommodated in the adjusting long hole 11.

It can be understood that the push button pressing block 33 is provided, so that the pushing component 31 can be conveniently and stably assembled on the support arm guard 20, that is to say, the pushing component 31 and the locking component 32 are assembled on the support arm guard 20. The arm long hole 22 is provided, so that the adjusting arm 10 can be extended into the arm long hole 22, the hole wall of the arm long hole 22 limits the adjusting arm 10 along the height direction and the width direction, and the telescopic adjusting mechanism 30 limits the adjusting arm 10 along the length direction. Specifically, the pressing block slot hole 21 is communicated with the arm long hole 22, the locking component 32 sequentially extends into the adjusting long hole 11 through the pressing block slot hole 21 and the arm long hole 22, and limits the hole wall of the adjusting long hole 11 along the length direction.

Further, as shown in FIGS. 2 to 5, in some embodiments, the pushing component 31 comprises a push button slider 311 and a push button resetting element 312. The push button slider 311 is slidably connected to the push button pressing block 33. A resetting element baffle 23 is provided on the outer side of the pressing block slot hole 21, and the push button resetting element 312 is provided between the push button slider 311 and the resetting element baffle 23.

It can be understood that the push button slider 311 is provided, so that the position of the locking component 32 is adjusted conveniently. Specifically, the position of the locking component 32 along the height direction is adjusted. The push button resetting element 312 and the resetting element baffle 23 are provided, so that the position of the push button slider 311 can be reset by the push button resetting element 312, and the locking component 32 can lock the adjusting arm 10. It should be noted that the locking component 32 locks the adjusting arm 10 when the push button resetting element 312 is in the original state, and the length of the knee brace 100 cannot be adjusted at this time. When it is necessary to adjust the length of the knee brace 100, the push button slider 311 is pushed, so that the push button resetting element 312 is gradually compressed. The locking component 32 is gradually unlocked from the adjusting arm 10 under the action of the push button slider 311, so that the adjusting arm 10 can move along the length direction with respect to the locking component 32 and the support arm guard 20, and the length of the knee brace 100 can be adjusted conveniently.

Figure 3:
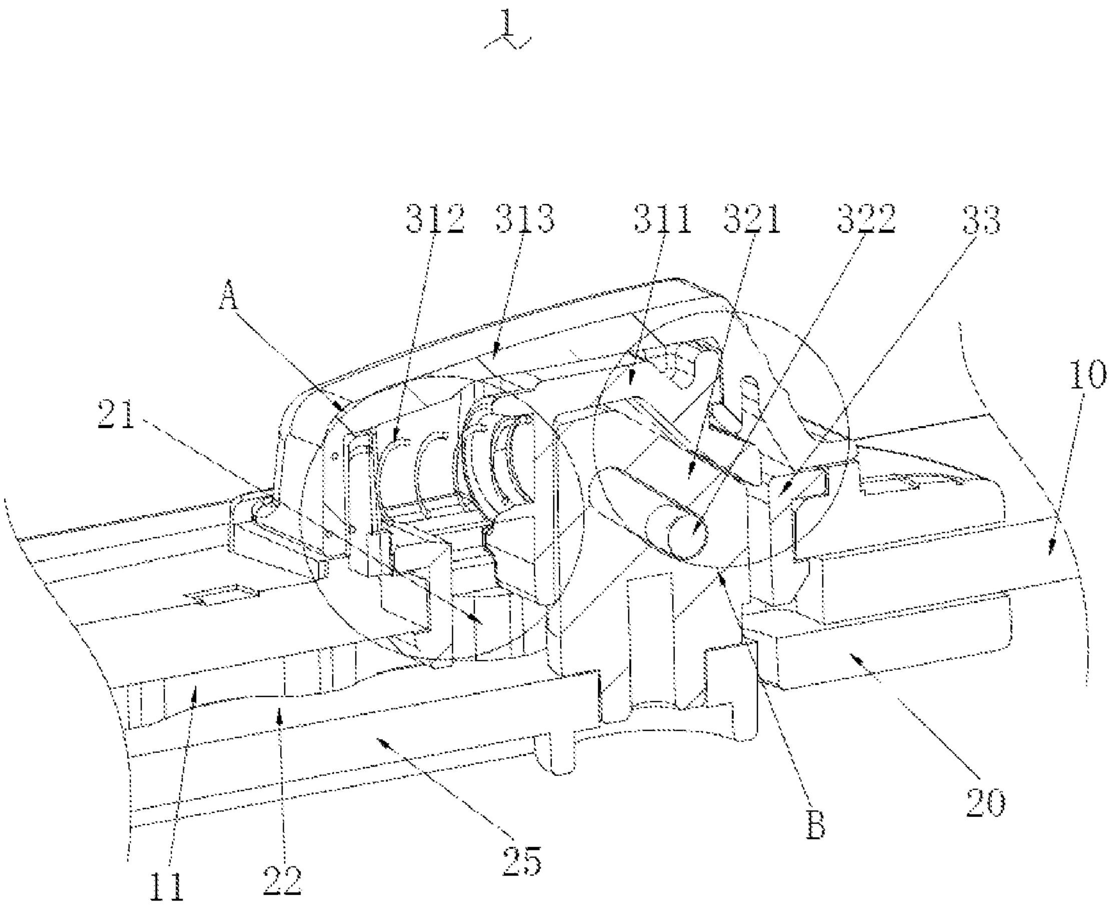
FIG. 3 is a partial three-dimensional cross-sectional schematic diagram of a telescopic adjusting structure of a support arm according to the present disclosure.
Figure 6:
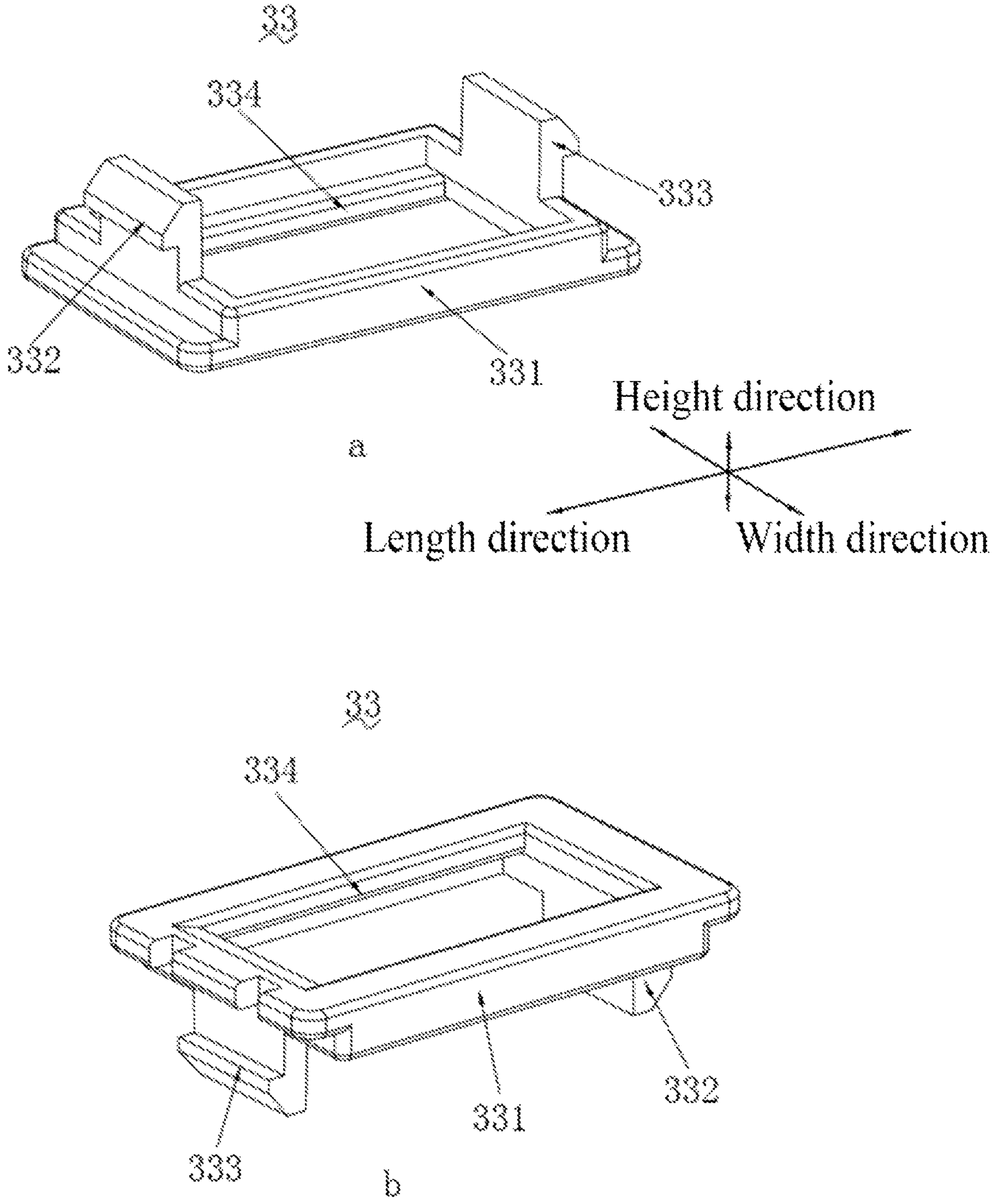
FIG. 6 is a three-dimensional structural schematic diagram of a push button pressing block of a pushing component of a telescopic adjusting structure of a support arm according to the present disclosure from two different perspectives.
Figure 7:
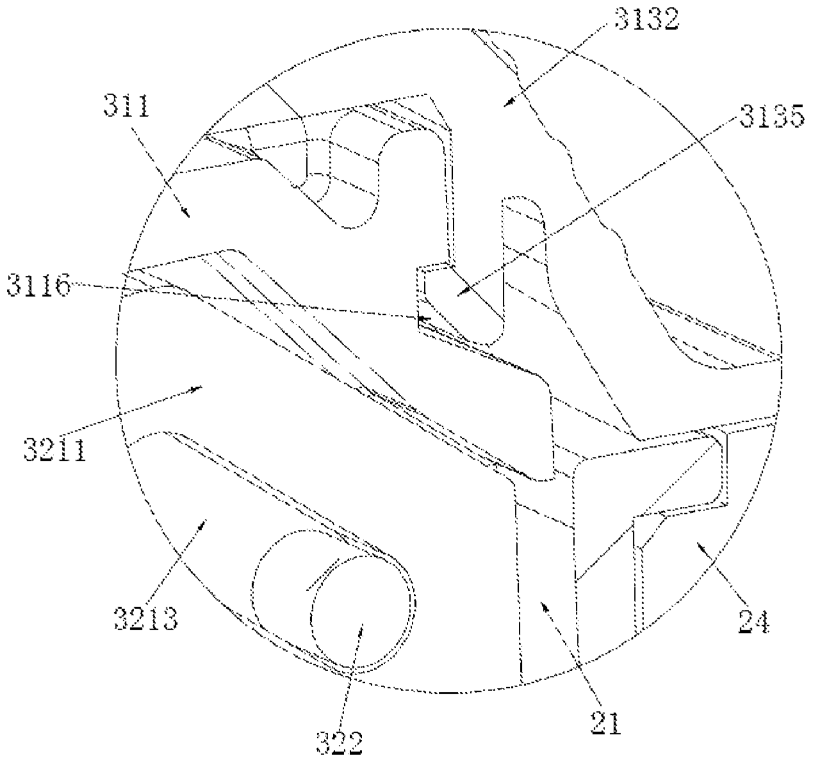
FIG. 7 is an enlarged schematic diagram of part B in FIG. 3 according to the present disclosure.

Further, as shown in FIG. 3, FIG. 6 and FIG. 7, figure a and figure b in FIG. 6 are three-dimensional structural schematic diagrams of the push button pressing block 33 from different perspectives. In some embodiments, the push button pressing block 33 comprises a pressing block frame body 331, a first arm guard connecting part 332, a second arm guard connecting part 333 and slider sliding rails 334. The pressing block frame body 331 is provided in the pressing block slot hole 21; the first arm guard connecting part 332 is provided at one end of the pressing block frame body 331 along the length direction; the second arm guard connecting part 333 is provided at the other end of the pressing block frame body 331 along the length direction; the slider sliding rails 334 are provided on two long sides of the pressing block frame body 331; wherein the first arm guard connecting part 332 and the second arm guard connecting part 333 are both clamped with the support arm guard 20, and the pushing component 31 is slidably connected with the slider sliding rail 334 and is limited with the slider sliding rail 334 along the upward direction in the height direction.

It can be understood that the pressing block frame body 331 is clamped on the support arm guard 20 by the first arm guard connecting part 332 and the second arm guard connecting part 333. The push button slider 311 is slidably connected with the slider sliding rail 334, and the slider sliding rail 334 is limited to move upward along the height direction by the push button slider 311, so that the slider sliding rail 334 is prevented from separating upward from the slider sliding rail 334 along the height direction. That is to say, the push button slider 311 is slidably connected with the slider sliding rail 334 and cannot be separated from the slider sliding rail 334 upward along the height direction. It is convenient to push the push button slider 311 and adjust the relative position of the locking component 32.

Figure 4:
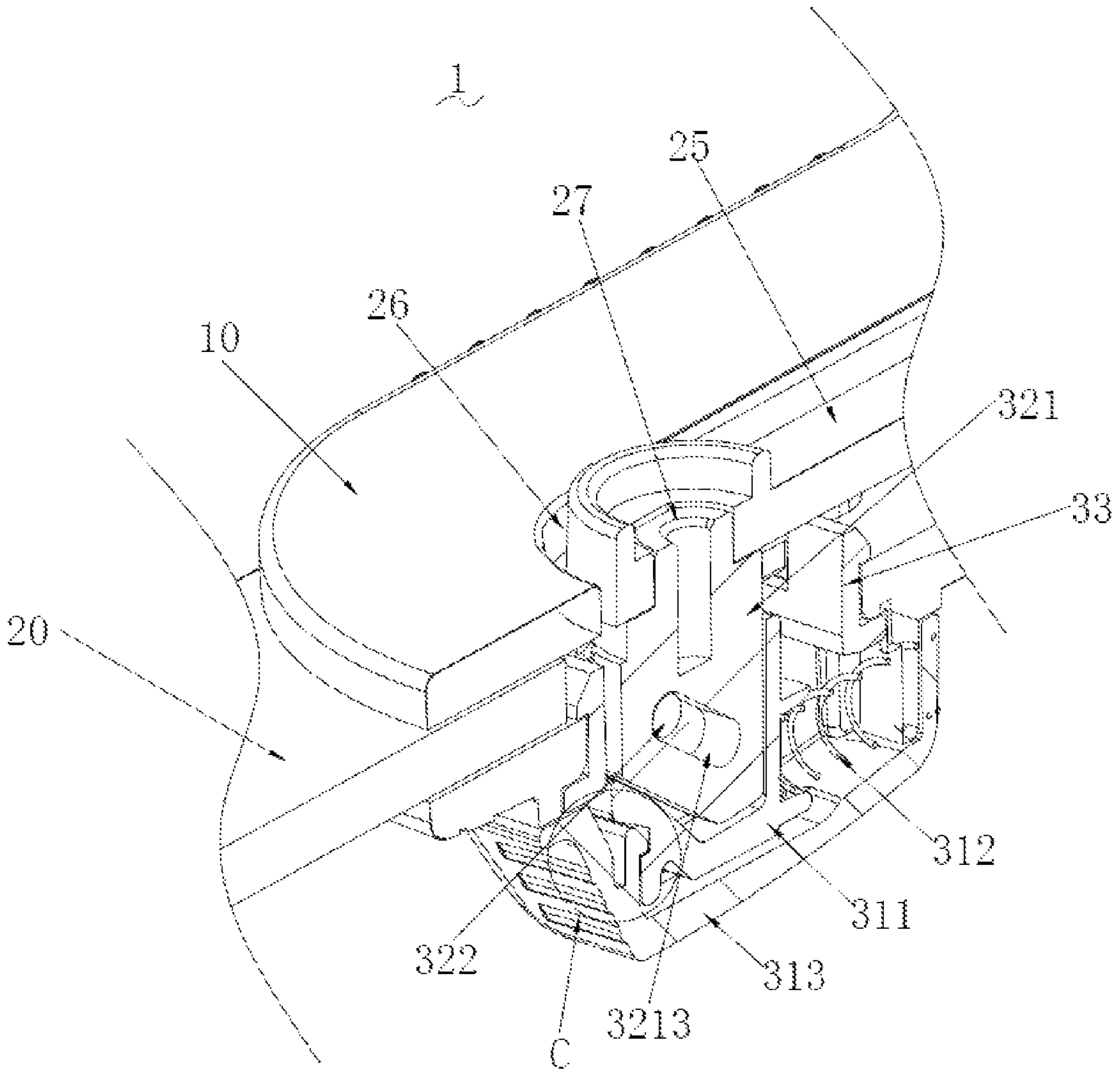
FIG. 4 is a partial three-dimensional cross-sectional schematic diagram of a telescopic adjusting structure of a support arm according to the present disclosure from another perspective.
Figure 5:
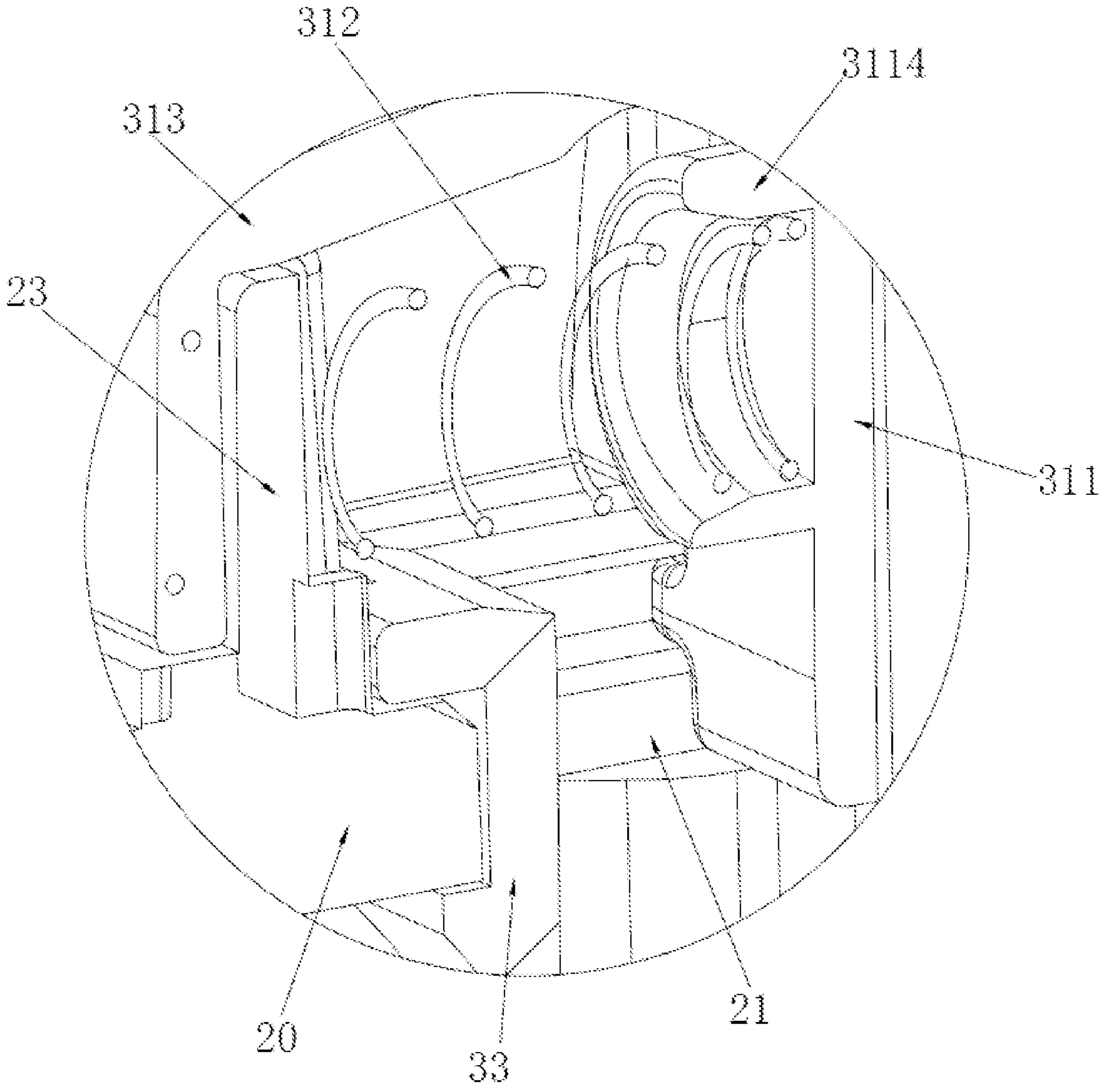
FIG. 5 is an enlarged schematic diagram of part A in FIG. 3 according to the present disclosure.
Figure 8:
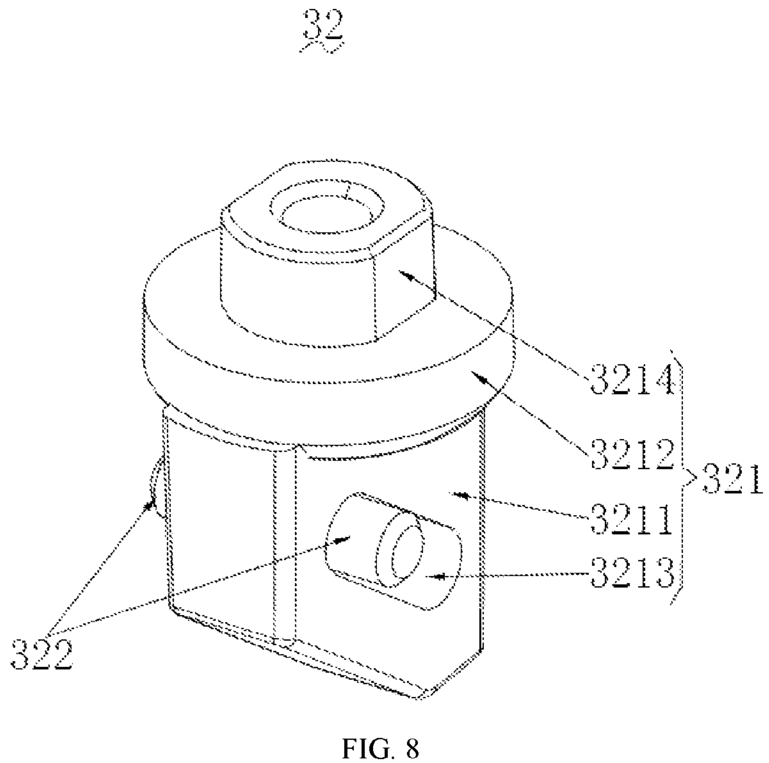
FIG. 8 is a three-dimensional structural schematic diagram of a locking component of a telescopic adjusting structure of a support arm according to the present disclosure.

Further, as shown in FIGS. 3, 4 and 8, in some embodiments, the locking component 32 comprises a push button stopper 321 and a push button stopper pin 322. One end of the push button stopper 321 is connected with the push button slider 311, and the other end of the push button stopper 321 is clamped with the adjusting arm 10. The push button stopper pin 322 is provided on the push button slider 311 and is clamped with the push button slider 311.

In the above embodiment, the push button stopper 321 is provided, so that the adjusting arm 10 is clamped and fixed by the push button stopper 321. At the same time, the relative position of the push button stopper 321 with respect to the adjusting arm 10 can be adjusted by the pushing component 31, so that the adjusting arm 10 is in a locked state or a free state along the length direction. The push button stopper pin 322 is provided, so that the push button stopper 321 can be connected with the push button slider 311, and the relative position of the push button stopper 321 can be conveniently adjusted by the push button slider 311. When in use, the user pushes the push button slider 311, and then the push button slider 311 drives the push button stopper 321 to move up and down through the push button stopper pin 322, so as to adjust the relative position between the push button stopper 321 and the adjusting arm 10, and further make the adjusting arm 10 in a locked state or a free state.

Figure 9:
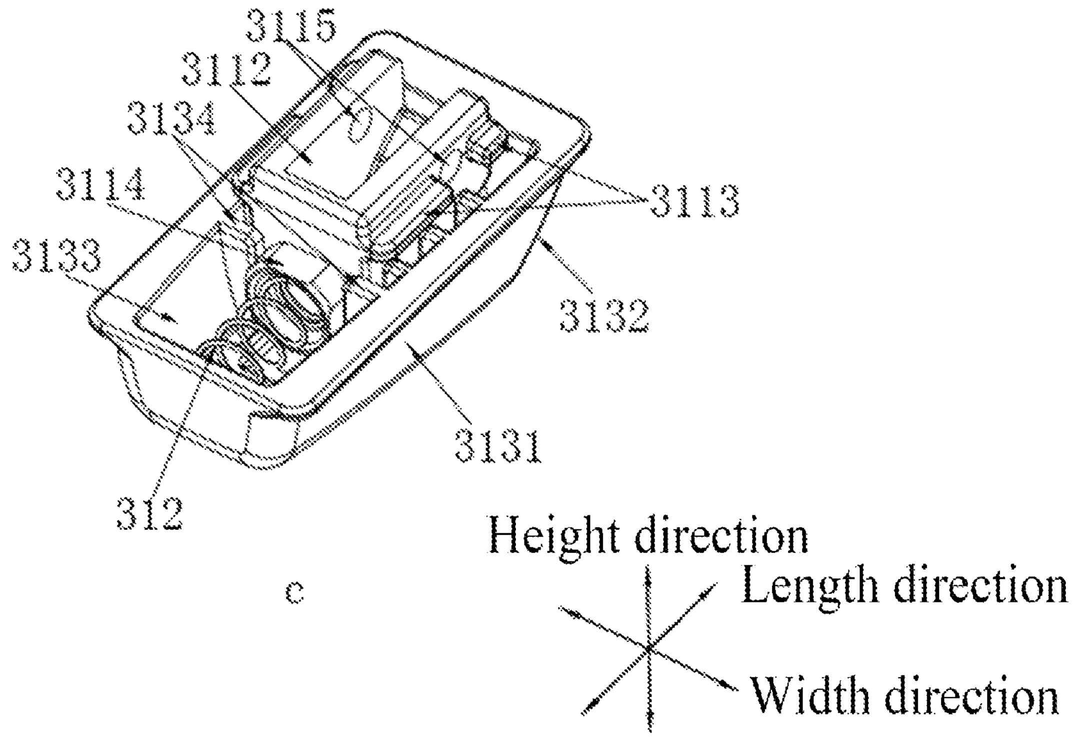
FIG. 9 is a three-dimensional structural schematic diagram of a pushing component of a telescopic adjusting structure of a support arm according to the present disclosure from two different perspectives.
Figure 9:
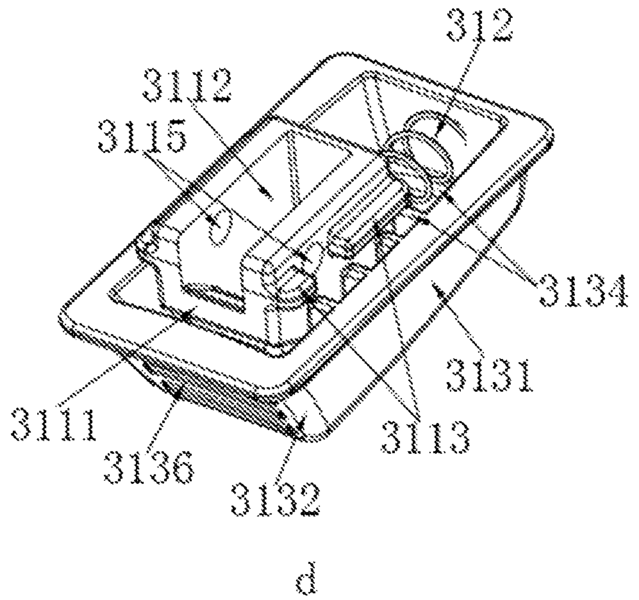
Figure 10:
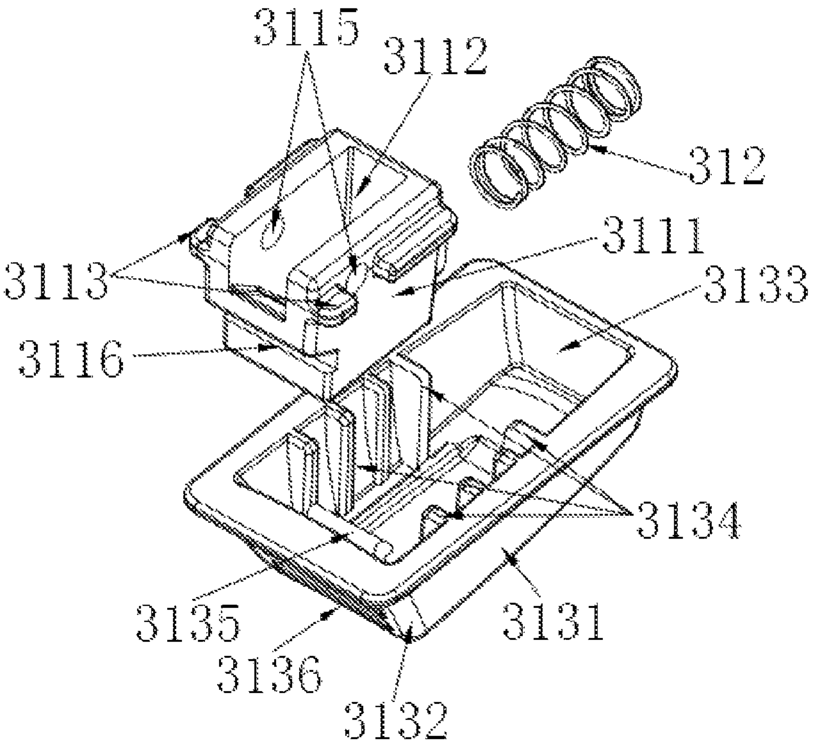
FIG. 10 is a three-dimensional explosion schematic diagram of a pushing component of a telescopic adjusting structure of a support arm according to the present disclosure.
Figure 11:
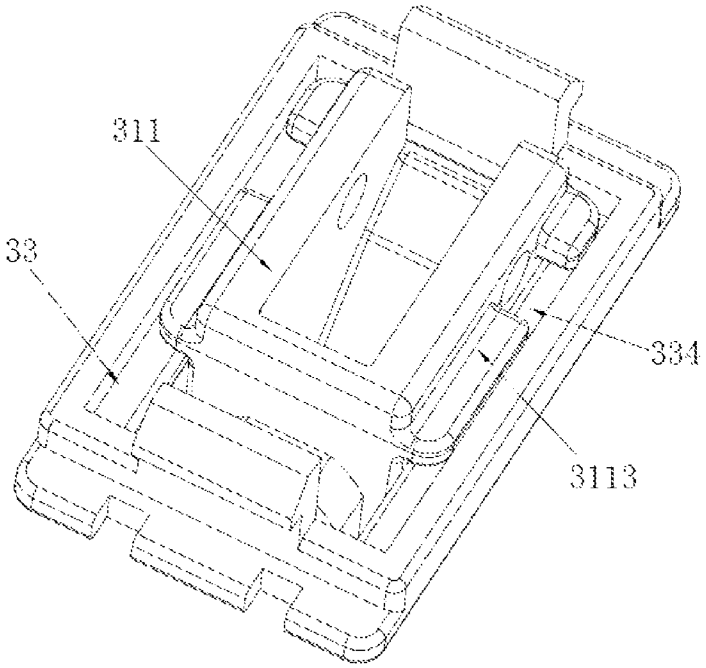
FIG. 11 is a three-dimensional schematic diagram of the cooperation relationship between a push button slider and a push button pressing block of a telescopic adjusting structure of a support arm according to the present disclosure.

Further, as shown in FIG. 9 to FIG. 11, figure c and figure d in FIG. 9 are three-dimensional schematic diagrams of the pushing component from different perspectives. In some embodiments, the push button slider 311 comprises a slider body 3111, a stopper accommodating groove 3112, a pressing block sliding rail 3113 and a resetting element fixing part 3114. The stopper accommodating groove 3112 is provided at one end of the slider body 3111 facing the push button stopper 321, and one end of the push button stopper 321 is clamped with the stopper accommodating groove 3112. The pressing block sliding rail 3113 is provided at both sides of the stopper accommodating groove 3112, and the pressing block sliding rail 3113 is slidably connected with the slider sliding rail 334. The resetting element fixing part 3114 is provided on the slider body 3111, and the push button resetting element 312 is provided between the resetting element fixing part 3114 and the resetting element baffle 23, wherein groove walls at both sides of the stopper accommodating groove 3112 along the length direction are provided with stopper pin fixing holes 3115, the push button stopper pin 322 penetrates through the push button stopper 321, and both ends of the push button stopper pin 322 are fixed in the stopper pin fixing holes 3115.

It can be understood that the stopper accommodating groove 3112 is provided, and the stopper pin fixing hole 3115 is provided thereon, so that the push button stopper pin 322 can be connected with the push button stopper 321, which provides a guarantee for conveniently adjusting the relative position of the push button stopper 321. The pressing block sliding rail 3113 is provided, so that the relative sliding between the slider body 3111 and the support arm guard 20 is convenient, and the moving track of the slider body 3111 is limited. It is ensured that the relative positional relationship between the locking component 32 and the adjusting arm 10 is effectively adjusted, and it is convenient to adjust the length of the knee brace 100.

Further, as shown in FIG. 9 to FIG. 11, in some embodiments, the pushing component 31 further comprises a push button slider cover 313. The push button slider cover 313 comprises a cover body 3131, a pushing end 3132, a slider accommodating groove 3133, a slider latch 3135 and a plurality of slider clamping blocks 3134. The pushing end 3132 is provided on the end of the cover body 3131 away from the resetting element baffle 23 along the length direction, and the pushing end 3132 is provided with skidproof stripes 3136. The slider accommodating groove 3133 is provided at one end of the cover body 3131 facing the support arm guard 20. The plurality of slider clamping blocks 3134 are provided at the inner groove wall of the slider accommodating groove 3133. The slider latch 3135 is provided at the groove wall of the slider accommodating groove 3133 close to the pushing end 3132. The push button slider 311 further comprises a cover body clamping groove 3116 provided at the side of the slider body 3111 away from the resetting element fixing part 3114, and the slider latch 3135 is clamped with the cover body clamping groove 3116. The plurality of slider clamping blocks 3134 cooperate with the slider latch 3135 to clamp and fix the cover body 3131 and the slider body 3111.

It can be understood that the push button slider cover 313 is provided, so that it is further convenient to operate the push button slider 311 to adjust the positional relationship of the push button stopper 321 with respect to the adjusting arm 10, which provides a guarantee for conveniently adjusting the length of the knee brace 100. The slider accommodating groove 3133, the slider clamping block 3134 and the slider latch 3135 are provided, so that the push button slider 311 can be conveniently accommodated, and the push button slider cover 313 can be prevented from accidentally falling off, thus ensuring the connection stability of the push button slider cover 313. During assembly, one end of the push button slider 311 away from the push button stopper 321 is clamped in the slider accommodating groove 3133, and the push button slider 311 is clamped and fixed by the cooperation of the slider clamping block 3134, the slider latch 3135 and the cover body clamping groove 3116.

Further, as shown in FIG. 9 and FIG. 10, in some embodiments, the push button stopper 321 comprises a slider connecting end 3211 and a limiting end 3212. The limiting end 3212 is integrally formed with the slider connecting end 3211. The adjusting arm 10 is provided with an adjusting long hole 11 along the length direction, a plurality of limiting parts 111 and accommodating parts 112 are provided in the adjusting long hole 11 at intervals, the size of the limiting parts 111 is smaller than that of the accommodating parts 112 along the width direction; the size of the slider connecting end 3211 along the width direction is smaller than that of the limiting part 111 along the width direction, and the size of the limiting part 111 along the width direction is smaller than that of the limiting end 3212 along the width direction; the slider connecting end 3211 is provided with a stopper pin sliding chute hole 3213, and the height of one side of the stopper pin sliding chute hole 3213 away from the resetting element baffle 23 is lower than that of one side of the stopper pin sliding chute hole 3213 close to the resetting element baffle 23; and the push button stopper pin 322 is slidably connected in the stopper pin sliding chute hole 3213.

It can be understood that the adjusting arm 10 is provided with an adjusting long hole 11, and a plurality of limiting parts 111 and accommodating parts 112 alternately provided at intervals in sequence are provided in the adjusting long hole 11. At the same time, the size relationship between the limiting parts 111 and accommodating parts 112 along the width direction is controlled. The size of the limiting part 111 along the width direction is smaller than that of the accommodating part 112 along the width direction. The size relationship between the slider connecting end 3211 and the limiting end 3212 and the limiting parts 111 along the width direction is controlled. Specifically, the size of the slider connecting end 3211 along the width direction is smaller than that of the limiting end 3212 along the width direction, and at the same time, the size of the slider connecting end 3211 along the width direction is smaller than that of the limiting part 111 along the width direction. The size of the limiting part 111 along the width direction is smaller than that of the limiting end 3212 along the width direction. That is to say, the sizes of the slider connecting end 3211, the limiting part 111 and the limiting end 3212 increase in sequence along the width direction. The limiting end 3212 is accommodated in the accommodating end when the push button resetting element 312 is in the original state. Further, the slider connecting end 3211 can pass through the limiting part 111, but the limiting end 3212 cannot pass through the limiting part 111. That is to say, the adjusting arm 10 is locked and limited along the length direction through the cooperation of the limiting end 3212 and the limiting part 111, and the free movement of the adjusting arm 10 along the length direction can be opened through the slider connecting end 3211.

At the same time, the stopper pin sliding chute hole 3213 is provided, so that the inclination angle of the stopper pin sliding chute hole 3213 is controlled. When the push button resetting element 312 is in the original state, the push button slider 311 and the push button slider cover 313 are in the original position. When the adjusting arm 10 is locked by the push button stopper 321 (that is to say, when the limiting end 3212 is accommodated in the accommodating part 112), the push button stopper pin 322 is located at the lowest end of the stopper pin sliding chute hole 3213. When the push button resetting element 312 is in a compressed state, the push button slider 311 and the push button slider cover 313 are pushed. When the adjusting arm 10 is not locked by the push button stopper 321 (that is to say, when the limiting end 3212 is disengaged from the accommodating part 112), the push button stopper pin 322 is disengaged from the lowest end of the stopper pin sliding chute hole 3213, and then the push button stopper 321 is pushed downward along the height direction to unlock the adjusting arm 10. In cooperation with the push button stopper pin 322, the displacement of the push button slider along the length direction is transmitted to the push button stopper, and the push button stopper moves up and down along the height direction, so as to adjust the positional relationship of the slider connecting end 3211 and the limiting end 3212 with respect to the limit part 111, and further adjust the push button stopper 321 to lock the adjusting arm 10, which provides a guarantee for conveniently adjusting the length of the knee brace 100.

Figure 12:
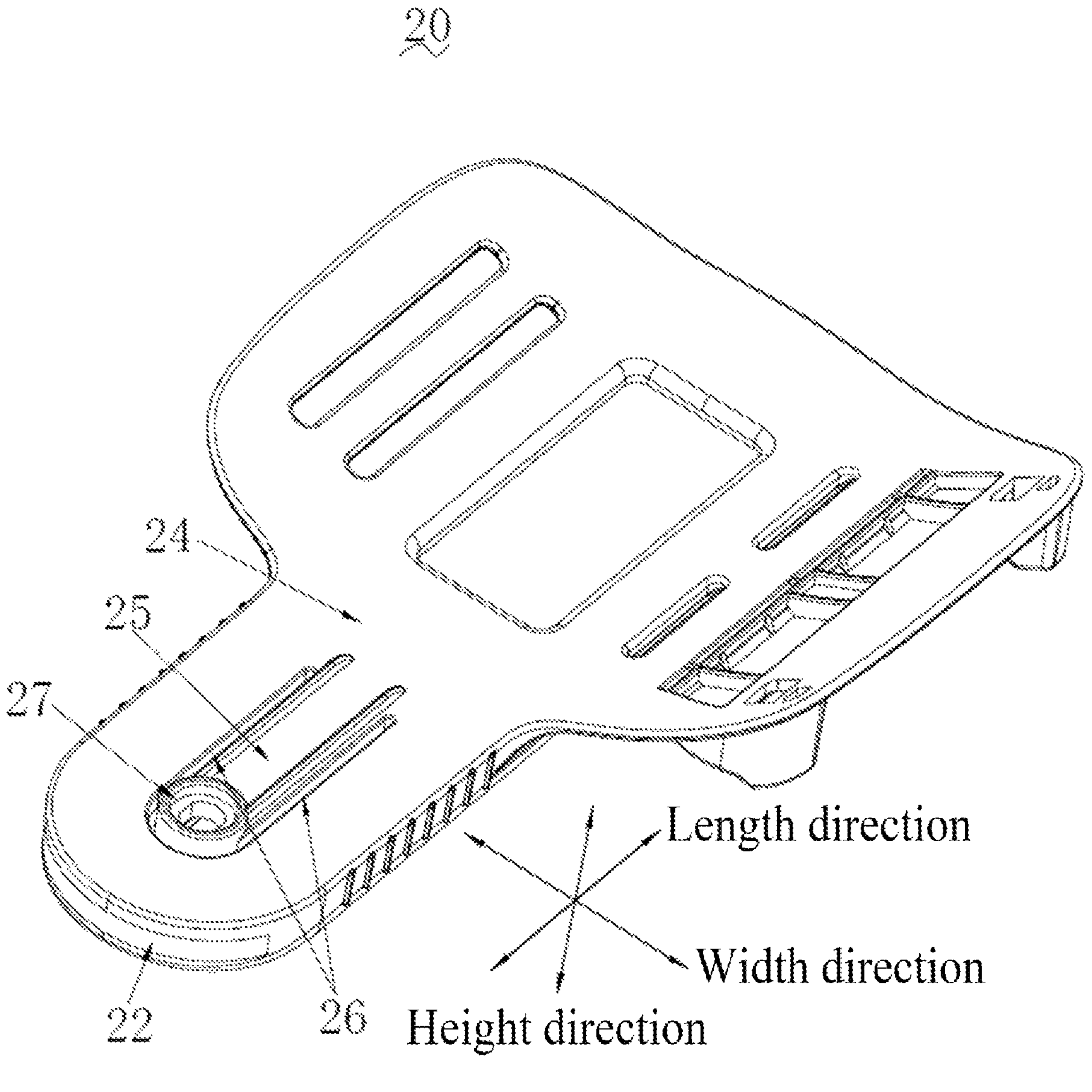
FIG. 12 is a three-dimensional structural schematic diagram of a support arm guard of a telescopic adjusting structure of a support arm according to the present disclosure.
Figure 13:
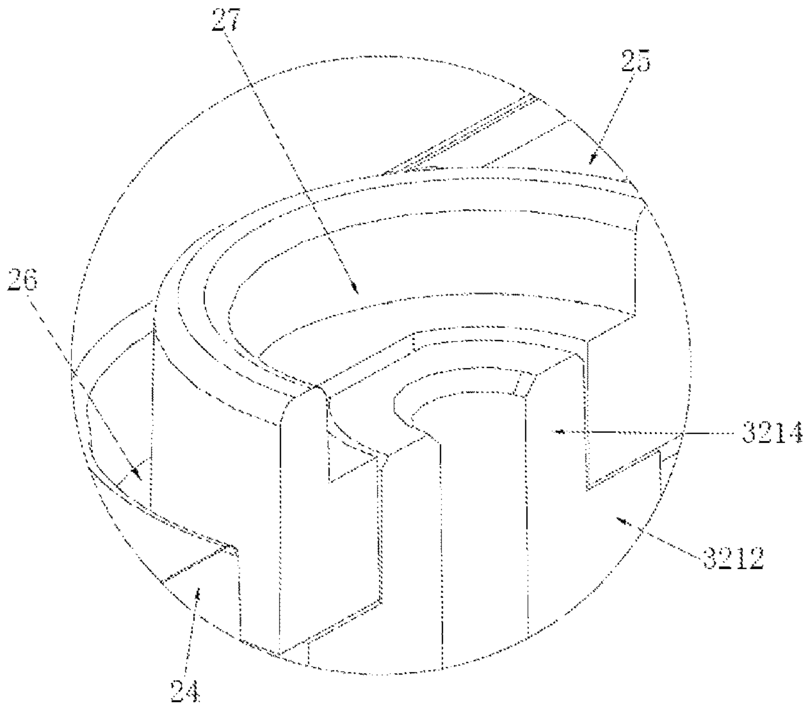
FIG. 13 is an enlarged schematic diagram of part C in FIG. 4 according to the present disclosure.

Further, as shown in FIG. 12 and FIG. 13, in some embodiments, the support arm guard 20 further comprises an arm guard body 24 and a stopper resetting and fixing cantilever 25. The arm long hole 22 and the pressing block slot hole 21 are both provided on the arm guard body 24, and the pressing block slot hole 21 is communicated with the arm long hole 22. The stopper resetting and fixing cantilever 25 is located on the arm guard body 24 below the pressing block slot hole 21, and a U-shaped slot hole 26 is provided between the stopper resetting and fixing cantilever 25 and the arm guard body 24. The stopper resetting and fixing cantilever 25 is provided with a threaded counterbore 27. Some of the limiting ends 3212 away from the slider connecting end 3211 extend with cantilever connecting parts 3214. The cantilever connecting parts 3214 abut against the threaded counterbore 27, and the cantilever connecting parts 3214 are screwed with the threaded counterbore 27 by screws.

In the above embodiment, the stopper resetting and fixing cantilever 25 is provided on the arm guard body 24, and a U-shaped slot hole 26 is controlled to be provided between the stopper resetting and fixing cantilever 25 and the arm guard body 24, so that the stopper resetting and fixing cantilever 25 has a certain elastic deformation ability. The threaded counterbore 27 is provided at one end of the stopper resetting and fixing cantilever 25 far away from the arm guard body 24. The limiting end 3212 extends out of the cantilever connecting parts 3214, and the cantilever connecting parts 3214 are screwed with the threaded counterbore 27 of the stopper resetting and fixing cantilever 25, so that the pushing component 31 and the locking component 32 are fixed between the push button pressing block 33 and the stopper resetting and fixing cantilever 25 along the height direction, and the push button resetting element 312 and the stopper resetting and fixing cantilever 25 cooperate to push the push button stopper 312 and the push button slider 311 to reset and lock the adjusting arm 10.

Figure 14:
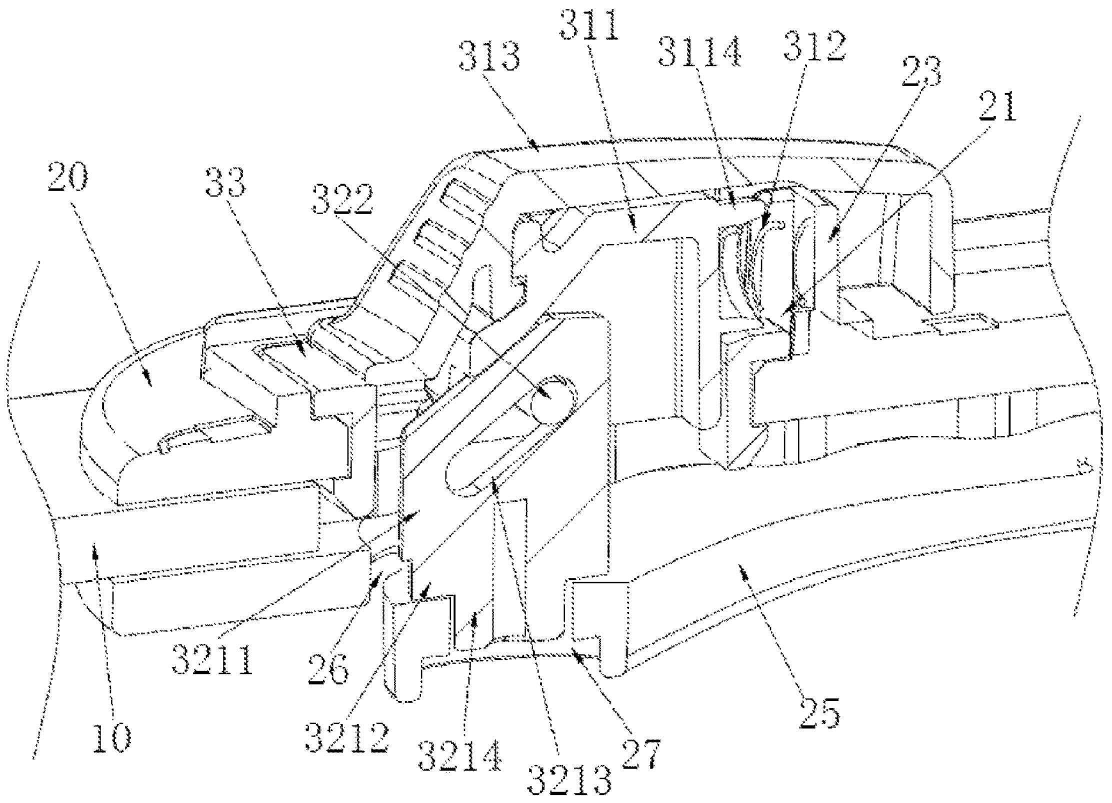
FIG. 14 is a partial three-dimensional cross-sectional schematic diagram of a telescopic adjusting structure of a support arm according to the present disclosure from another perspective.

Further, as shown in FIG. 3, FIG. 4 and FIG. 14, in some specific embodiments, the locking component 32 locks the support arm in a normal state. When adjusting the length of the knee brace 100 through the telescopic adjusting structure 1 of the support arm, the user pushes the pushing end 3132 of the push button slider cover 313 along the length direction. The thrust of the user can be effectively transmitted to the cover body 3131 under the action of the skidproof stripe 3136, and then is transmitted to the slider body 3111 under the action of the slider clamping block 3134, the slider latch 3135 and the cover body clamping groove 3116.

Subsequently, the slider body 3111 transmits the thrust to the push button resetting element 312 through the resetting element fixing part 3114. The push button resetting element 312 includes but is not limited to a spring and an elastic sheet. At the same time, the stopper pin fixing hole 3115 is in cooperation with the push button stopper pin 322 and the stopper pin sliding chute hole 3213, so that the thrust in the length direction is converted into a downward thrust along the height direction, and acts on the push button stopper 321. The push button stopper 321 moves downward after being stressed, so that the limiting end 3212 is separated from the accommodating part 112 of the adjusting long hole 11 of the adjusting arm 10 downward along the height direction. In this way, the slider connecting end 3211 reaches the area of the accommodating part 112 along the height direction. Subsequently, the adjusting arm 10 is in a state of free movement along the length direction because the size of the slider connecting end 3211 along the width direction is smaller than that of the limiting part 111. The user can conveniently adjust the relative position between the adjusting arm 10 and the support arm guard 20, and further adjust the length of the knee brace 100.

It should be pointed out that when the limiting end 3212 of the push button stopper 321 is disengaged from the accommodating part 112 downward along the height direction, the limiting end 3212 synchronously pushes the stopper resetting and fixing cantilever 25 to elastically deform downward. That is to say, when the adjusting arm 10 is in a state of free movement along the length direction, the push button slider cover 313, the push button slider 311 and the push button stopper 321 are simultaneously subjected to reaction forces from the push button resetting element 312 and the stopper resetting and fixing cantilever 25, and these two reaction forces can effectively help the locking component 32 to lock the adjusting arm 10 again. It should be noted that the scale identification 113 is provided outside the adjusting long hole 11 of the adjusting arm 10, which not only facilitates the user to adjust the length of the knee brace 100, but also serves as the identification of the areas of the accommodating part 112 and the limiting part 111, and facilitates the user to stop the slider connecting end 3211 at the accommodating part 112 every time when adjusting the relative position of the adjusting arm 10 and the support arm guard 20 (it is only limited to stay in the accommodating part 112 at a time, which will not result in the problem that the length of the knee brace 100 is not properly adjusted). It is convenient for the limiting end 3212 to be reset to the accommodating part 112.

After the user adjusts the length of the knee brace 100, the pushing end 3132 of the push button slider cover 313 is released. The slider body 3111 is reset along the length direction under the action of the reset elastic force of the push button resetting element 312 and the stopper resetting and fixing cantilever 25. The limiting end 3212 of the push button stopper 321 is reset to the accommodating part 112 along the height direction, locking and limiting the movement of the adjusting arm 10 along the length direction again, thus completing the automatic reset of the pushing component 31 and the locking component 32 and further improving the convenience of adjusting the length of the knee brace 100.

In a second embodiment of the present disclosure, a knee brace 100 is further provided, which comprises two telescopic adjusting structures of the support arms 1 as described above. It can be understood that the knee brace

100 according to the present disclosure uses the telescopic adjusting structure 1 of the support arm in the above embodiment of the present disclosure, so as to conveniently and quickly adjust the length of the knee brace 100.

To sum up, the present disclosure provides a telescopic adjusting structure of a support arm and a knee brace. The telescopic adjusting structure of the support arm is used for a support arm of a knee brace and comprises an adjusting arm and a support arm guard movably connected along the length direction. The telescopic adjusting structure further comprises a telescopic adjusting mechanism, and the telescopic adjusting mechanism comprises: a pushing component, which is movably provided on the support arm guard; a locking component, one end of which is connected with the pushing component, and the other end of which is clamped with the adjusting arm, wherein when the pushing component moves, the locking component is disengaged from or locked with the adjusting arm. The telescopic adjusting mechanism is provided, so that the extension length matching between the adjusting arm and the support arm guard can be adjusted.

The telescopic adjusting mechanism is provided with the pushing component and the locking component, so that the position of the locking component is adjusted by the pushing component, and the adjusting arm is locked and fixed by the locking component. At the same time, the pushing component is provided on the support arm guard and is connected with the locking component, so that the relative positions of the support arm guard and the adjusting arm can be adjusted by the pushing component and the locking component. In this way, the pushing component can be operated so as to adjust the locking component to lock the adjusting arm, so that the length of the support arm of the knee can be adjusted conveniently and quickly.

It should be understood that the application of the present disclosure is not limited to the above examples. For those skilled in the art, improvements or transformations can be made according to the above description, and all these improvements and transformations should belong to the protection scope of the appended claims of the present disclosure.

What is claimed is:

1. A telescopic adjusting structure of a support arm, which is used for a support arm of a knee brace and comprises an adjusting arm and a support arm guard movably connected along the length direction, wherein the telescopic adjusting structure further comprises a telescopic adjusting mechanism, and the telescopic adjusting mechanism comprises:

a pushing component, which is movably provided on the support arm guard, wherein the support arm guard is provided with a pressing block slot hole, and the pushing component is provided in the pressing block slot hole;

a locking component, one end of which is connected with the pushing component, and the other end of which is clamped with the adjusting arm, wherein when the pushing component moves, the locking component is disengaged from or locked with the adjusting arm;

wherein the pushing component comprises a push button slider, which is slidably accommodated in the pushing component; and a push button resetting element, wherein a resetting element baffle is provided at the outer side of the pressing block slot hole of the support arm guard, and the push button resetting element is provided between the push button slider and the resetting element baffle.

2. The telescopic adjusting structure of the support arm according to claim 1, wherein the telescopic adjusting mechanism further comprises:

a push button pressing block;

wherein the support arm guard is provided with an arm long hole along the length direction, the adjusting arm is slidably connected in the arm long hole, the adjusting arm is provided with an adjusting long hole along the length direction, and one end of the locking component away from the pushing component is accommodated in the adjusting long hole.

3. The telescopic adjusting structure of the support arm according to claim 2, wherein the push button slider is slidably connected to the push button pressing block.

4. The telescopic adjusting structure of the support arm according to claim 1, wherein the push button pressing block comprises:

a pressing block frame body, which is provided in the pressing block slot hole;

a first arm guard connecting part, which is provided at one end of the pressing block frame body along the length direction;

a second arm guard connecting part, which is provided at the other end of the pressing block frame body along the length direction;

slider sliding rails, which are provided on two long sides of the pressing block frame body;

wherein the first arm guard connecting part and the second arm guard connecting part are both clamped with the support arm guard, and the pushing component is slidably connected with the slider sliding rail and is limited with the slider sliding rail along the upward direction in the height direction.

5. The telescopic adjusting structure of the support arm according to claim 4, wherein the locking component comprises:

a push button stopper, one end of which is connected with the push button slider, and the other end of which is clamped with the adjusting arm;

a push button stopper pin, which is provided on the push button slider and is clamped with the push button slider.

6. The telescopic adjusting structure of the support arm according to claim 5, wherein the push button slider comprises:

a slider body;

a stopper accommodating groove, wherein the stopper accommodating groove is provided at one end of the slider body facing the push button stopper, and one end of the push button stopper is clamped with the stopper accommodating groove;

a pressing block sliding rail, which is provided at both sides of the stopper accommodating groove and is slidably connected with the slider sliding rail;

a resetting element fixing part, wherein the resetting element fixing part is provided on the slider body, and the push button resetting element is provided between the resetting element fixing part and the resetting element baffle;

wherein groove walls at both sides of the stopper accommodating groove along the length direction are provided with stopper pin fixing holes, the push button stopper pin penetrates through the push button stopper, and both ends of the push button stopper pin are fixed in the stopper pin fixing holes.

7. The telescopic adjusting structure of the support arm according to claim 6, wherein the pushing component further comprises a push button slider cover, and the push button slider cover comprises:

a cover body;

a pushing end, which is provided at one end of the cover body away from the resetting element baffle along the length direction and is provided with skidproof stripes;

a slider accommodating groove, which is provided at one end of the cover body facing the support arm guard;

a plurality of slider clamping blocks, which are provided at the inner groove wall of the slider accommodating groove;

a slider latch, wherein the slider latch is provided at the groove wall of the slider accommodating groove close to the pushing end, the push button slider further comprises a cover body clamping groove provided at one side of the slider body away from the resetting element fixing part, and the slider latch is clamped with the cover body clamping groove;

wherein the plurality of slider clamping blocks cooperate with the slider latch to clamp and fix the cover body and the slider body.

8. The telescopic adjusting structure of the support arm according to claim 6, wherein the push button stopper comprises:

a slider connecting end;

a limiting end, which is integrally formed with the slider connecting end;

wherein the adjusting arm is provided with an adjusting long hole along the length direction, a plurality of limiting parts and accommodating parts are provided in the adjusting long hole at intervals, the size of the limiting parts is smaller than that of the accommodating parts along the width direction; the size of the slider connecting end along the width direction is smaller than that of the limiting part along the width direction, and the size of the limiting part along the width direction is smaller than that of the limiting end along the width direction; the slider connecting end is provided with a stopper pin sliding chute hole, and the height of one side of the stopper pin sliding chute hole away from the resetting element baffle is lower than that of one side of the stopper pin sliding chute hole close to the resetting element baffle; and the push button stopper pin is slidably connected in the stopper pin sliding chute hole.

9. The telescopic adjusting structure of the support arm according to claim 8, wherein the support arm guard further comprises:

an arm guard body, wherein the arm long hole and the pressing block slot hole are both provided on the arm guard body, and the pressing block slot hole is communicated with the arm long hole;

a stopper resetting and fixing cantilever, wherein the stopper resetting and fixing cantilever is located on the arm guard body below the pressing block slot hole, and a U-shaped slot hole is provided between the stopper resetting and fixing cantilever and the arm guard body;

wherein the stopper resetting and fixing cantilever is provided with a threaded counterbore, some of the limiting ends away from the slider connecting end extend with cantilever connecting parts, the cantilever connecting parts abut against the threaded counterbore, and the cantilever connecting parts are screwed with the threaded counterbore by screws.

10. A knee brace, comprising the telescopic adjusting structure of the support arm according to claim 1.

* * * * *